United States Patent [19]

Baudino et al.

[11] Patent Number: 4,791,935
[45] Date of Patent: Dec. 20, 1988

[54] OXYGEN SENSING PACEMAKER

[75] Inventors: Michael D. Baudino, Coon Rapids; Michael D. de Franco, Blaine; Joseph F. Lessar, Coon Rapids; Dennis A. Brumwell, Bloomington, all of Minn.; Gene A. Bornzin, Camarillo, Calif.; Jeffrey A. Schweitzer, Minneapolis, Minn.

[73] Assignee: Medtronic, Inc., Minneapolis, Minn.

[21] Appl. No.: 896,695

[22] Filed: Aug. 15, 1986

[51] Int. Cl.⁴ .............................................. A61N 1/00
[52] U.S. Cl. .................................. 128/637; 128/692; 128/633
[58] Field of Search ............... 128/633, 634, 785, 786, 128/673, 675, 692

[56] References Cited

U.S. PATENT DOCUMENTS

| | | | |
|---|---|---|---|
| 3,057,356 | 10/1962 | Greatbatch | 128/422 |
| 3,349,762 | 10/1967 | Kapany | 128/2.05 |
| 3,358,690 | 12/1967 | Cohen | 128/419 |
| 3,478,746 | 11/1969 | Greatbatch | 128/421 |
| 3,593,718 | 7/1971 | Krasner et al. | 128/419 P |
| 3,902,501 | 9/1975 | Citron et al. | 128/418 |
| 4,009,721 | 3/1977 | Alcidi | 128/419 PG |
| 4,140,132 | 2/1979 | Dahl | 128/419 PG |
| 4,191,193 | 3/1980 | Seo | 128/675 |
| 4,201,219 | 5/1980 | Bozal | 128/419 PG |
| 4,202,339 | 5/1980 | Wirtzfeld et al. | 128/419 PG |
| 4,252,124 | 2/1981 | Mauer et al. | 128/635 |
| 4,269,198 | 5/1981 | Stokes | 128/785 |
| 4,379,462 | 4/1983 | Borkan et al. | 128/786 |
| 4,399,820 | 8/1983 | Wirtzfeld et al. | 128/419 PG |
| 4,407,296 | 10/1983 | Anderson | 128/675 |
| 4,413,636 | 11/1983 | Jasso | 128/786 |
| 4,432,372 | 2/1984 | Monroe | 128/675 |
| 4,437,475 | 3/1984 | White | 128/785 |
| 4,467,807 | 8/1984 | Bornzin | 128/419 PG |
| 4,481,953 | 11/1984 | Gold et al. | 128/786 |
| 4,485,813 | 12/1984 | Anderson et al. | 128/675 |
| 4,487,206 | 12/1984 | Aagard | 128/673 |
| 4,523,279 | 6/1985 | Sperinde et al. | 364/416 |
| 4,554,927 | 11/1985 | Fussell | 128/673 |
| 4,600,017 | 7/1986 | Schroeppel | 128/675 |

OTHER PUBLICATIONS

Article entitled "An Integrated Circuit-Based Optical Sensor for in vivo Measurement of Blood Oxygenation", authored by Joseph M. Schmitt et al, published in IEEE Transactions on Biomedical Engineering, vol. BME-33, No. 2, Feb. 1986.

Article entitled "A Proposed Miniature Red/Infrared Oximeter Suitable for Mounting on a Catheter Tip", authored by Sinclair Yee et al, published in IEEE Transactions on Biomedical Engineering, vol. BME-24, No. 2, 1977.

Article entitled "A Light Emitting Diode Skin Reflectance Oximeter", authored by A. Cohen et al, published in Medical and Biological Engineering, vol. 10, pp. 385-391, 1972.

Article entitled "The Theory and Construction of Oximeters", authored by W. J. Reichert, published in Int. Anesth. Clin., vol. 44, Spring 1966.

Article entitled "A New Instrument for Rapid Measurement of Blood Oxygen Saturation and Hb Concentration", author unknown, published in Biomedical Engineering, vol. 5, 1970.

Article entitled "The Principle Design and Features of a New Hb-Oximeter", authored by F. J. Janssen, published in Medical & Biological Engineering, vol. 10, pp. 9-22, 1972.

Primary Examiner—Francis J. Jaworski
Assistant Examiner—George Manuel
Attorney, Agent, or Firm—Reed A. Duthler; Joseph F. Breimayer; John J. Rooney

[57] ABSTRACT

A heart pacemaker including a two wave length reflectance oximeter for determining oxygen saturation. The pacing rate is increased or decreased in response to the measured oxygen saturation. By appropriate multiplexing and timing functions, the two wave length reflectance oximeter is included in a pacing lead coupled to the pacemaker which requires only three conductors.

5 Claims, 8 Drawing Sheets

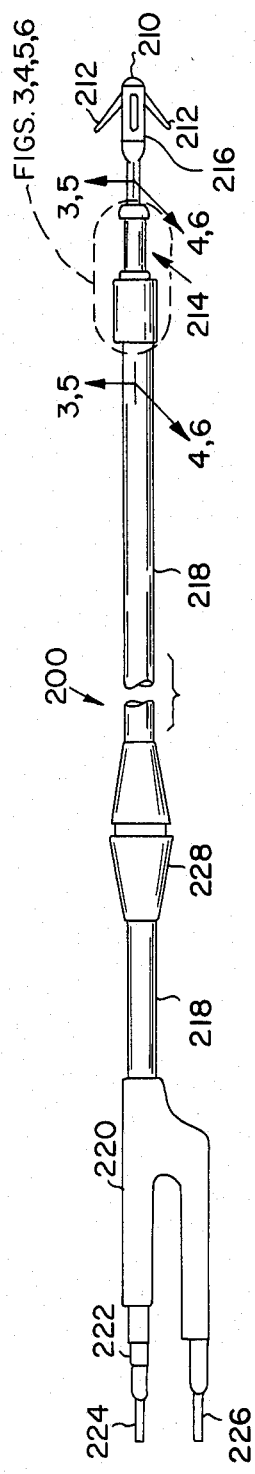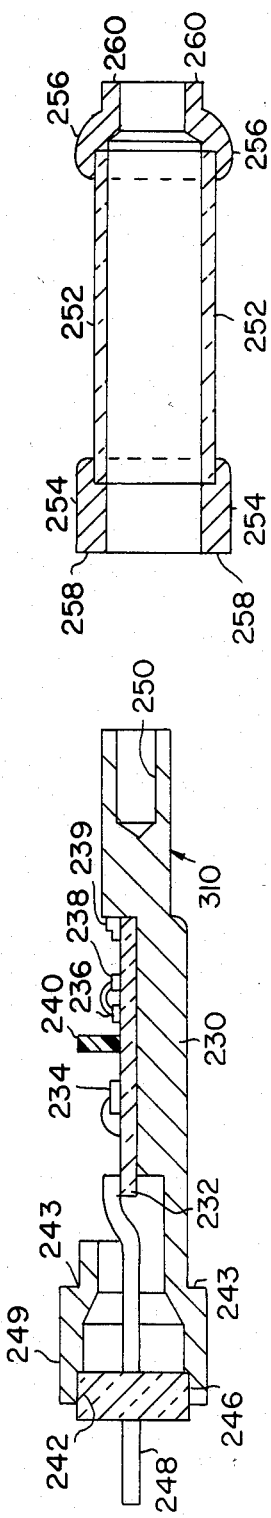

OXYGEN SENSING PACEMAKER

BACKGROUND OF THE INVENTION

The present invention relates generally to medical devices and more specifically relates to implantable electronic devices for muscle stimulation.

The earliest implantable pacing systems operated asynchronously to normal physiologic functions. U.S. Pat. No. 3,057,356; issued to Greatbatch, teaches such a pacemaker which includes a fixed rate oscillator which determines an escape interval. At the expiration of each escape interval, a pacing pulse is generated. Subsequent designs, such as in U.S. Pat. No. 3,478,746 issued to Greatbatch, incorporated a sense amplifier coupled to the pacing electrode, which sensed the electrical activity indicative of a contraction of the heart and reset the oscillator to restart timing the escape interval. These pacemakers, called demand pacemakers, only paced if no natural contractions were sensed within the escape interval.

As an alternative to regulating pacing rate by sensing the contractions of the heart, some pacemakers have regulated rate in response to measurement of some other, physiological parameter. There have been pacemakers proposed which vary rate in accordance to instantaneous blood pressure within the right atrium, as in U.S. Pat. No. 3,358,690, in response to respiration as in U.S. Pat. No. 3,593,718, in response to physical activity as in U.S. Pat. No. 4,140,132 or in response to neurological activity as in U.S. Pat. No. 4,201,219 The most promising techniques appear to involve varying of pacing rate in response to sensing of chemical parameters of the blood. For example, U.S. Pat. No. 4,009,721 and U.S. Pat. No. 4,252,124 teach pacemakers in which an implantable pH sensor determines the rate of the pacing oscillator. U.S. Pat. No. 4,202,339 issued to Wirtzfeld and U.S. Pat. No. 4,399,820 issued to Wirtzfeld et al, both teach a pacing system in which the rate of an asynchronous pacing oscillator is controlled by the oxygen level of the intracardiac venous blood. U.S. Pat. No. 4,467,807 issued to Bornzin combines the techniques of varying the rate of the pacemaker in response to sensed oxygen with the demand function, so that an interaction of both of these factors determines the delivery of pacing impulses by the pacemaker.

SUMMARY OF THE INVENTION

The present invention comprises an improved oxygen sensor and associated circuitry for use within a cardiac pacemaker of the type in which pacing rate is dependent upon the percentage of oxygen saturation of the intracardiac venous blood. The present invention includes a hermetically sealed sensor capsule containing a two wavelength reflectance oximeter. The method of construction of this capsule assures its suitability for long term human implant. In addition, the invention includes timing, processing and output circuitry for operating the sensor in a predetermined time relationship with pacing output pulses and which allows the construction of a long term implantable lead which performs EKG sensing, cardiac pacing and two wave length reflectance oximetry using only three conductors. Minimizing the number of conductors is believed particularly valuable in long term implantable devices, where experience has shown that electronic complexity is preferable to mechanical complexity.

The invention will be more readily and easily understood in conjunction with the following detailed description.

BRIEF DESCRIPTION OF THE DRAWINGS

FIG. 2 is a plan view of a pacing and oxygen sensing lead according to the present invention.

FIG. 3 is a side sectional view of the sensor body, a subassembly of the sensor capsule.

FIG. 4 is a side sectional view of the window assembly, a subassembly of the sensor capsule.

DETAILED DESCRIPTION OF THE DRAWINGS

Figure 1:
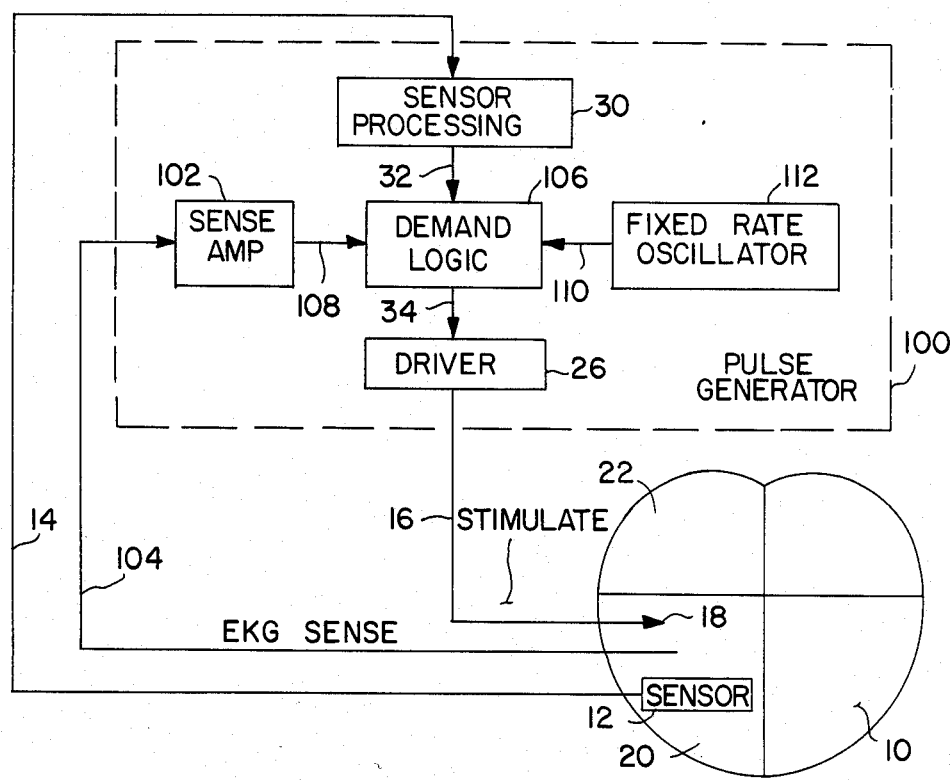
FIG. 1 is an illustration of a prior art rate adaptive demand pacemaker in which sensed oxygen saturation is used to regulate the pacing rate.

FIG. 1 illustrates a rate adaptive demand pacemaker in which sensed oxygen level is used to vary the escape interval of a demand pacemaker, as disclosed in U.S. Pat. No. 4,467,807 issued to Bornzin, and incorporated herein by reference in its entirety. This figure is intended both to illustrate pertinent prior art in this area and to provide a general illustration of how the circuitry and sensor of the present invention would be functionally related to the circuitry of an implantable pacemaker.

FIG. 1 shows a single chamber pacing system including a sensor 12 within the right ventricle 20 of heart 10, which generates a voltage on line 14 proportional to percentage of oxygen saturation in the right ventricle of the heart. The voltage on line 14 is processed by sensor processing circuitry 30 which includes an analog to digital converter which converts the voltage on line 14 to a binary number which is used to control the pacing rate set by demand logic 106 and fixed rate oscillator 112. Line 104 is coupled to an electrode in right ventricle 20 of the heart 10 and delivers electrical signals to the sense amp 102 which generates an output on line 108 indicative of the sensing of a natural contraction of the human heart. On sensing such a contraction, the timing period of the demand logic is reset. On expiration of the escape interval determined by demand logic 106 and fixed rate oscillator 112 under the control of sensor processing 30, a signal is generated on line 34 which triggers driver 26 to produce a stimulating pulse via line 16, to be applied to an electrode 18 within the right ventricle of the heart 10. A detailed description of the circuitry employed in sensor processing block 30 and demand logic 106 can be found in U.S. Pat. No. 4,467,807 at column 3, lines 59-68, column 4, lines 1-68 and column 5, lines 1-30.

Although the incorporation of the present invention in an implantable pacemaker is discussed specifically with reference to the pacemaker disclosed in FIG. 1, the invention is believed equally applicable to other pacemakers employing alternate circuitry configurations for determining rate in response to an analog signal indicative of oxygen saturation. For example, it is believed the invention would also be useful in conjunction with a pacemaker as disclosed in U.S. Pat. No. 4,202,339 issued to Wirtzfeld, cited above.

FIG. 2 is a plan view of a permanently implantable lead according to the present invention. Lead 200 is provided with a pacing electrode 210 at its extreme distal tip, which is held in place within the heart by tines 212, which may be of the type described in U.S. Pat. No. 3,902,501 issued to Citron et al or U.S. Pat. No. 4,269,198 issued to Stokes and incorporated herein by reference in their entirety. Located proximal to electrode 210 is sensor capsule 214, which contains a two reflectance oximeter. Capsule 214 is spaced from electrode 210 by an insulative lead body 216 which encloses a conductor which couples electrode 210 to sensor capsule 214. Proximal to sensor 214 is an elongated lead body 218 which is preferably sheathed in a pliant, insulative material such as polyurethane or silicone rubber. Lead body 218 contains three coaxially mounted coiled conductors coupled to sensor capsule 214 and extending to connector assembly 220. Connector assembly 220 includes three connector surfaces 222, 224, and 226 which are coupled to the three conductors mounted within lead body 218. An anchoring sleeve 228 is optionally included to stabilize lead 200 at the point of venous insertion. Anchoring sleeve 228 may be of the type described in U.S. Pat. No. 4,437,475 issued to White.

FIG. 3 is a side sectional view of the sensor body assembly, a subassembly of the sensor capsule 214 of the present invention. The sensor body assembly includes a machined titanium sensor body 230 provided with a distal end 310 of circular cross section and a proximal end 249, also of circular cross section. The sensor body 230 also has longitudinal surface 231 which serves to mounted the ceramic substrate 232 upon which the various electronic elements of the two frequency reflectance oximeter are located. These elements include a phototransistor 234, an infrared light emitting diode 236 and a red light emitting diode 238. Diodes 236 and 238 are separated from phototransistor 234 by a semicircular wall 240. At the proximal end of sensor body 230 is an aperture 242 in which a sapphire or glass feedthrough 246 is located. Feedthrough 246 has been brazed to sensor body 230 around its entire circumference, using a braze such as gold. Extending through and also brazed to feedthrough 246 are two wires, of which only one, labeled 248, is visible in this view. Wire 248 is soldered to a conductive pad located on ceramic 232. At the distal end of sensor body 230 is a bore 250 which serves as a mounting point for a coiled conductor.

FIG. 4 is a side sectional view of the window assembly of the sensor capsule. The window assembly includes an optically pure sapphire or glass circular cylindrical tube 252 and two welding collars 254 and 256 located at the proximal and distal ends, respectively, of tube 252. Welding collars 254 and 256 are fabricated of titanium. Welding collars 254 and 256 are provided with lumens which have circular cross sections and are provided with circumferential indentations at the distal and proximal ends, respectively, which receive the ends of sapphire tube 252. Welding collars 254 and 256 are brazed to the proximal and distal ends of sapphire tube 252 around their entire circumference, using a braze which is preferably gold. Prior to brazing, the proximal and distal ends of tube 252 are coated with a thin film of niobium or similar metalization to facilitate brazing. Vapor deposition or sputtering techniques may be used to provide this thin film.

The capsule itself is assembled by sliding the window assembly of FIG. 4 proximally over the body assembly of FIG. 3, until the proximal end 258 of weld collar 254 is adjacent the shoulder 243 of sensor body 230 (FIG. 3). The inner diameter of the proximal portion 258 of weld collar 254 is the same as the outer diameter of the distal portion 310 of the sensor body 230. The inner diameter of the distal end of the lumen of weld collar 256 is approximately equal to the outer diameter of the distal end 310 of sensor body 230. The inner diameter of the lumen of weld collar 254 is approximately equal to the outer diameter of the sensor body 230 immediately distal to shoulder 243. After assembly, weld collar 254 and weld collar 256 may conveniently be laser welded to sensor body 230, around the circumference of proximal end 258 of weld collar 254 and of distal, end 260 of weld collar 256. The circular cross sections of weld collars 254 and 256 and of sensor body 230 at the weld point simplifies the weld process by allowing the assembly to simply be rotated under the welding beam. Laser welding is the preferred method, but other methods such as electron beam welding may also be appropriate. This procedure produces a hermetically sealed sensor capsule appropriate for a long term implant within the human body. The use of titanium for both the sensor body 230 and for the weld collars 254 and 256 prevents any corrosion at the weld. The interrelation of the sensor capsule to the remainder of the components of the lead is described below in FIGS. 5 and 6.

Figure 5:
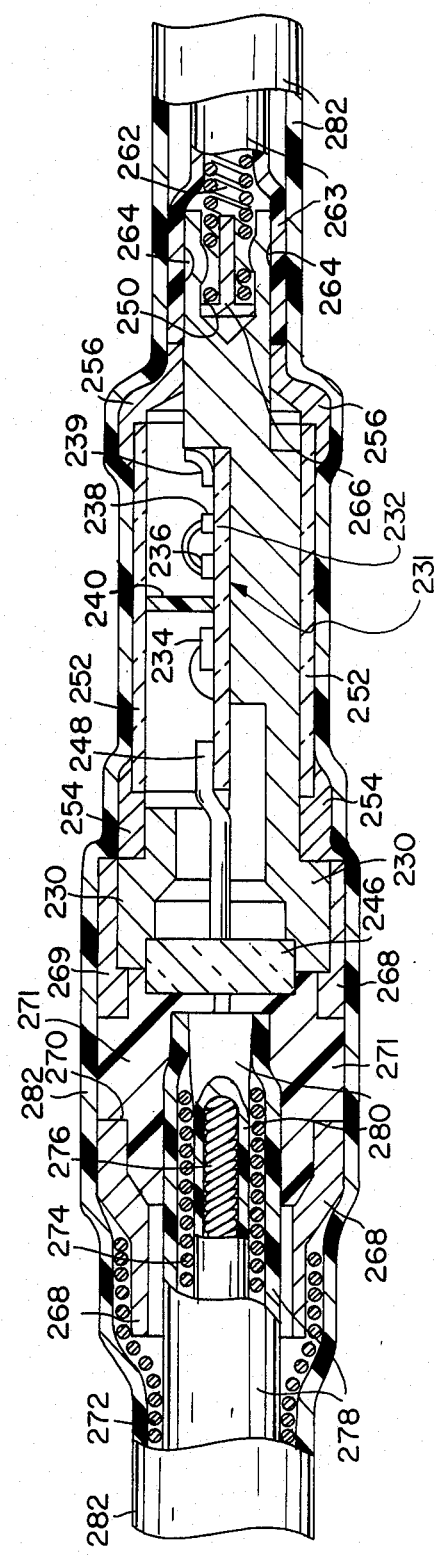
FIG. 5 is a side sectional view through the completed sensor capsule.

FIG. 5 is a side sectional view of the sensor capsule, mounted in the lead of FIG. 2. Within bore 250 at the distal end of sensor body 230 is located a coiled conductor 262 which is held in place by crimps 264 which mechanically an electrically couple it to sensor body 230. Conductor 262 extends to and is electrically coupled with tip electrode 210 (FIG. 2).

At the proximal end of the sensor body is a capsule adapter 268, which is laser welded at its distal end to sensor body 230 and welding collar 254. Capsule adapter 268 is generally cylindrical and hollow in its construction, and includes a cross bore 270 for addition of backfill material 271. Welded to capsule adapter 268 is a coiled conductor 272, which is coupled to connector pin 226 (FIG. 2). Located within the internal cavity 269 of adapter 268 are two, mutually insulated coaxially coiled conductors including coiled conductor 274 and coiled conductor 276, which are insulated by insulating sheaths 278 and 280, respectively. Conductor 276 is attached to wire 248, within a welding sleeve, not visible in this illustration. Conductor 274 is coupled to a second wire, passing through feedthrough 246. The entire lead is sheathed in an outer insulative sheath 282, which is preferably fabricated of polyurethane or other transparent, non-thrombogenic material. Cavity 269 is backfilled with epoxy 271. All other labeled elements correspond to identically numbered elements in FIGS. 3 and 4, above.

Figure 6:
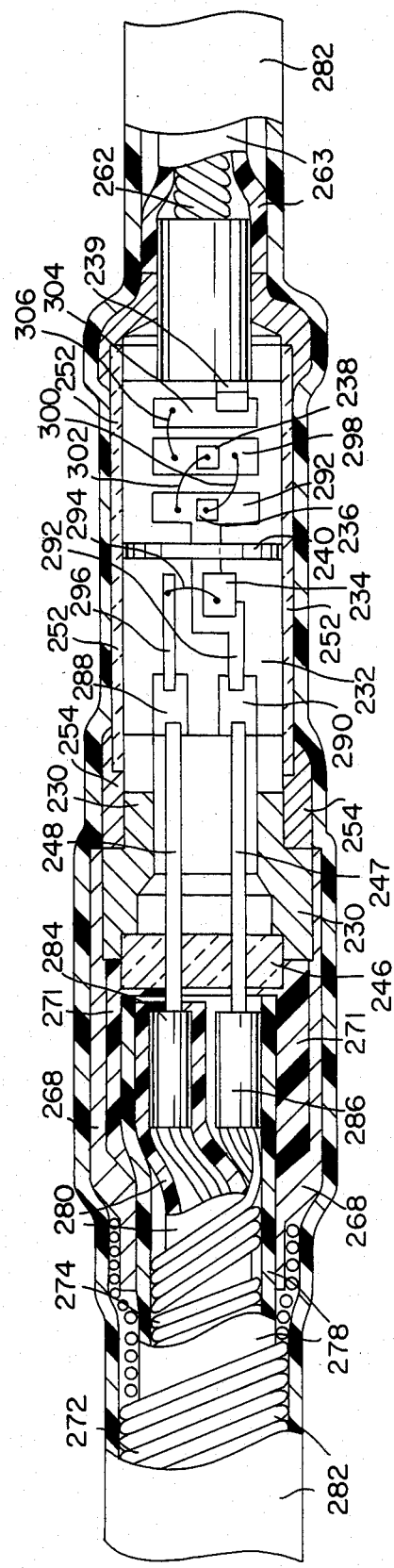
FIG. 6 is a top sectional view through the completed sensor capsule.

FIG. 6 is a top cut away vie of the sensor capsule mounted in the lead of FIG. 2. In this view, the connection of conductors 274 and 276 to wire 248 and 247 is clearly visible. Conductors 274 and 276 are preferably multifilar coils which are welded to wires 247 and 248, and mounted within welding sleeves 284 and 286. In this view, it can be seen that wires 247 and 248 are coupled to two metallic pads 288 and 290 on substrate 232. Phototransistor 234 is seen to be mounted on a conductive path 292, coupled to metallic pad 290. Phototransistor 234 is coupled by means of a fine wire 294 to a second conductive path 296, coupled to metallic pad 288. Conductive path 292 extends under wall 240, and serves as the mounting point for infrared LED 236. A third conductive path 298 serves at a mounting point for red LED 238. LED's 236 and 238 are connected to pads 292 and 298, respectively, by means of fine wires 300 and 302. Conductive path 298 is coupled to a fourth conductive path 304 by means of a fine wire 306 and is coupled to sensor body 230 by metallic strap 239. All other elements correspond to identically numbered elements in FIGS. 3, 4 and 5.

Figure 7:
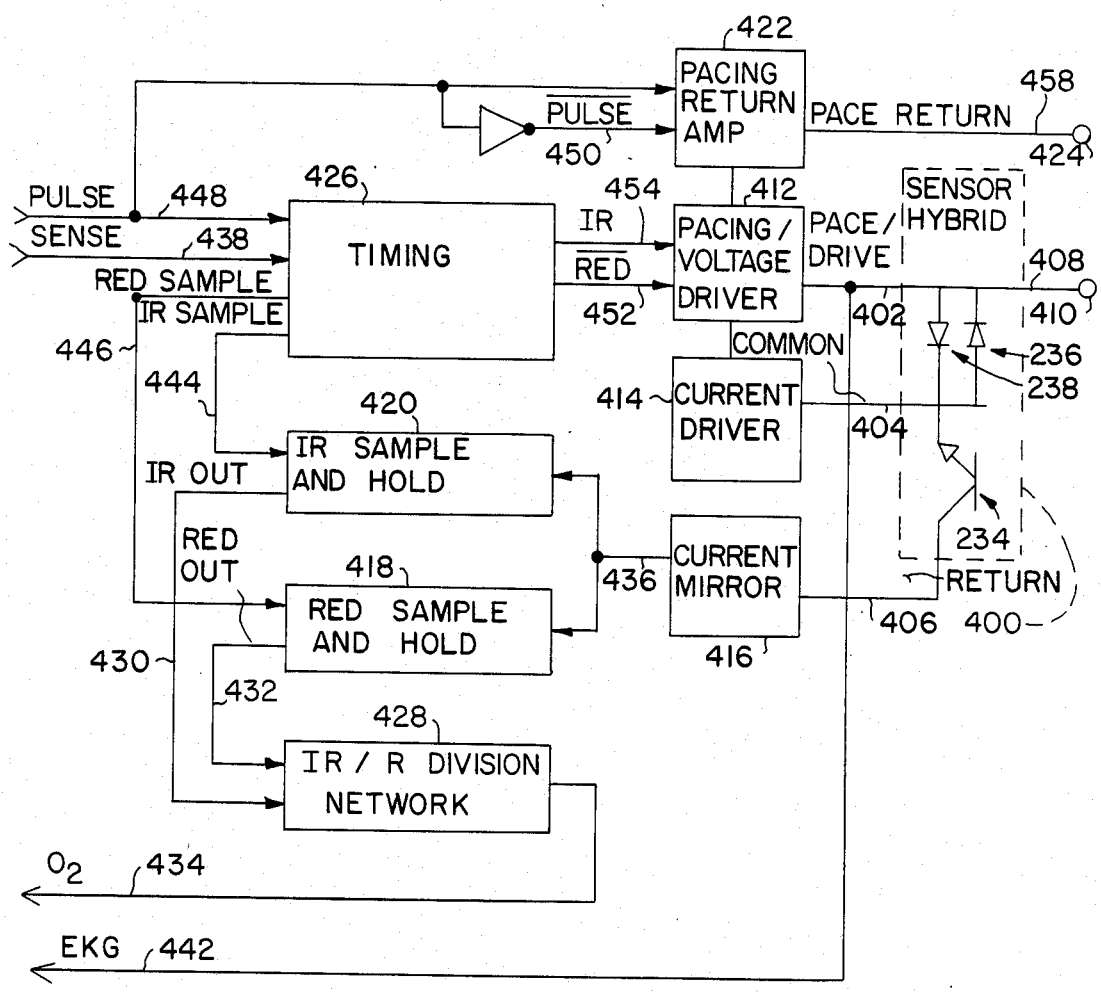
FIG. 7 is a functional diagram of the sensor and associated circuitry.

FIG. 7 is a functional diagram of the sensor and its associated circuitry. In this view, the sensor hybrid 400 is illustrated schematically, showing the interconnection of infrared LED 236, red LED 238 and phototransistor 234. The three lines 402, 404 and 406 correspond to coiled conductors 272, 274 and 276, respectively, in FIGS. 5 and 6. Line 408 corresponds to conductor 262, shown in FIG. 5 and electrode 410 corresponds to tip electrode 210, shown in FIG. 2.

The diode pair 236 and 238 is driven by a pair of push pull amplifiers 412 and 414. Amplifier 112 operates in a voltage output mode, and amplifier 414 operates in a current output mode. The returning current from phototransistor 234 is converted to a proportional DC voltage by the current mirror 416 and is delivered to the sample and hold switches 418 and 420 which recover the peak signal for each color. Pacing is accomplished by placing line 402 from voltage driver 412 at a logic 0 and placing line 458 to return amplifier 422 at a logic 1. For example, if the system employs a 3.6 volt lithium thionylchloride cell, this produces a pacing voltage of approximately 3.1 volts across the heart. Pacing return amplifier 422 is coupled to electrode 424, which may conveniently be the metal enclosure of the implanted pacemaker. Timing for the entire system is provided by integrated circuitry included in the timing block 426, which controls the timing and function of the pacing voltage driver 412 and the current driver 414 as well as determining times for operation of the sample and hold circuits 418 and 420. The outputs of sample and hold circuits 418 and 420 are coupled to a division network 428 which divides the output of IR sample and hold 420, on line 330 by the output of red sample and hold 418 on line 432 to produce a D.C. voltage signal on line 434 indicative of the percentage of oxygen saturation. IR/R division network 428 may be of the type illustrated in FIG. 1 of U.S. Pat. No. 4,202,339 issued to Wirtzfeld et al and incorporated herein in its entirety. In particular, it may correspond to the division network labeled 16, and described in column 3, lines 30–36. Line 434, carrying an analog signal indicative of oxygen saturation may be coupled to the sensor processing circuitry of a pacemaker such as illustrated in FIG. 1. The sensor and associated circuitry may replace the sensor 12 and line 14 of FIG. 1, with the output of IR/R division network 428 functionally coupled to sensor processing circuitry 30.

The functional interconnection of the circuitry of FIG. 7 with the remainder of the circuitry of an implantable cardiac pacemaker is also described in conjunction with the prior art pacemaker illustrated in FIG. 1. Sensor operation under control of timing circuit 426 may conveniently be initiated in response to a signal on line 448 indicative of the occurrence of a cardiac pacing pulse or a signal on line 438 indicative of a sensed spontaneous contraction of the heart. The input to timing 426 on line 448 therefore might be functionally coupled to the output of demand logic 106 on line 34 and the input to timing 426 on line 438 might be functionally coupled to the output of sense amplifier 102 on line 108. Return pacing amp 422 may be functionally coupled to demand logic 106 so as to be activated by a signal on line 448 indicative of time out of the escape interval. Finally, electrode 410 may be coupled via line 442 to the input sense amp 102 on line 104 so that electrode 410 also acts as an EKG sensing electrode.

Figure 8:
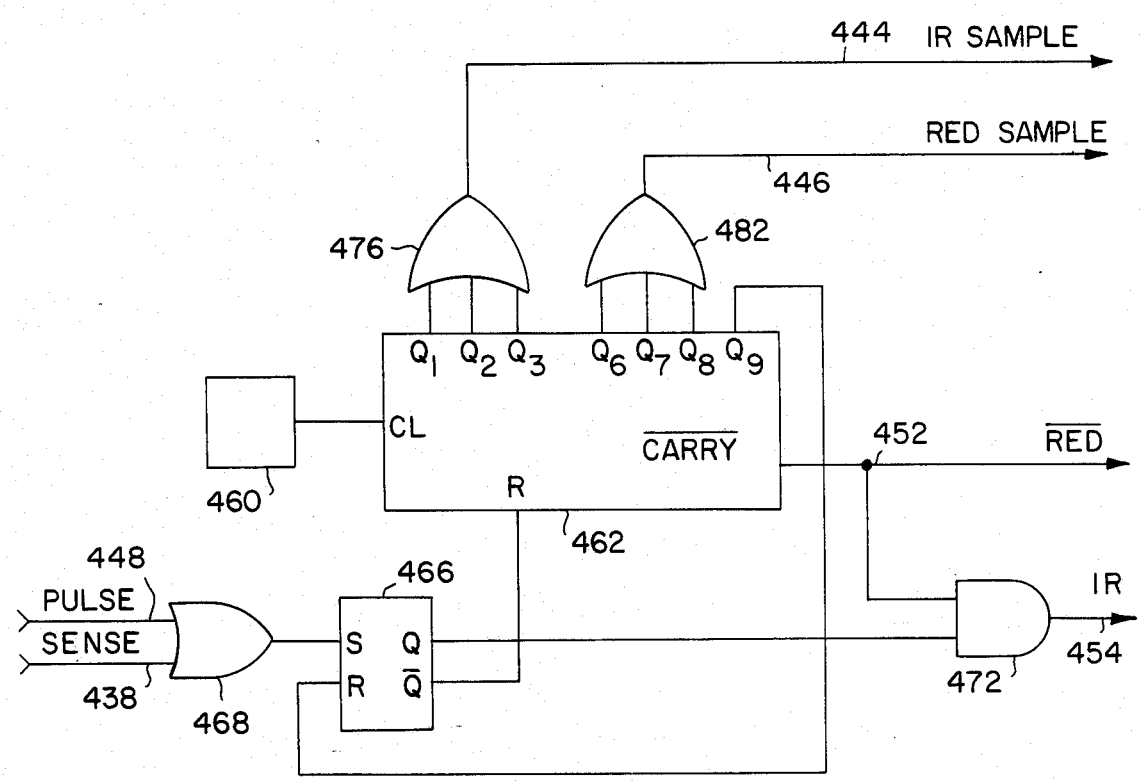
FIG. 8 is a circuit diagram of the analog circuitry associated with the sensor.

FIG. 8 is a schematic of a timing circuit for use with the sensor lead of FIGS. 2–6. Decade counter 462 serves to time the application of current to the infrared and red LEDs in the sensor capsule as well as defining sampling periods during the operation of the red and infrared LEDs. The basic operation is as follows: Following a signal on line 438 or 448 indicative of a sensed contraction of the heart or a delivered pacemaker pulse, set-reset flip-flop 466 is reset via NOR gate 468, which removes the reset from counter 462, allowing it to be clocked by 10 Khz clock 460, and driving the signal on IR line 454 to a logic 1 via AND gate 472. When the signal on line 454 is high, current is applied to activate the infrared LED 236. During counts 1, 2 and 3 of decade counter 462, the IR SAMPLE line 444 is driven to a logic 1 via NAND gate 476. During counts 1, 2 and 3, the IR sample and hold circuitry is activated. At a count of 5, the CARRY output of decade counter 462 goes to a logic 0, driving the signal on the RED line 452 to logic 0, and also driving the signal on IR line 454 to a logic 0 via AND gate 472. While the signal on RED line 452 is at a logic 0, current is applied to drive the red LED. During counts 6, 7 and 8 of decade counter 462, the RED SAMPLE line 446 goes to a logic 1, via OR gate 482. During counts 6, 7 and 8, the red sample and hold circuitry is activated. On a count of 9, the set reset flip-flop 466 is reset, locking decade counter 462 on reset and driving RED line 452 high, ending delivery of current to the red LED. Thus, this circuitry provides timing for driving the infrared and red LEDs in sequence, and sampling each diode during the center portion of the period during which they are driven. This sequence of events occurs a fixed time after either a pulse signal on line 448 or a sense signal on line 438, which assures that the oxygen level is sampled once per each heartbeat, without running the risk of attempting to sense the oxygen level during a pacing pulse or resetting the pulse generator timing in response to electrical currents driven through the sensor.

Figure 9:
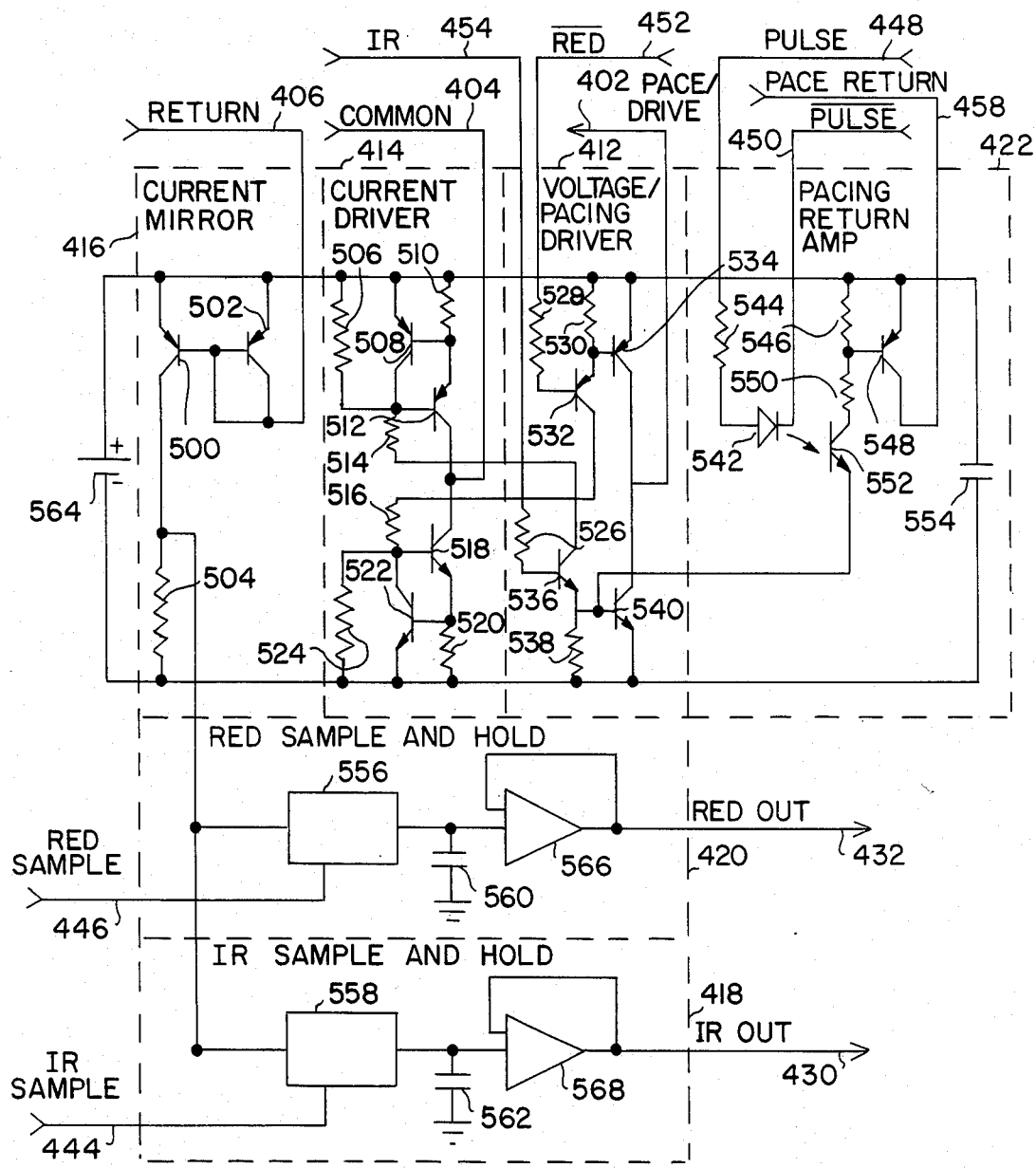
FIG. 9 is a schematic of the digital timing circuitry associated with the sensor capsule.
Figure 10:
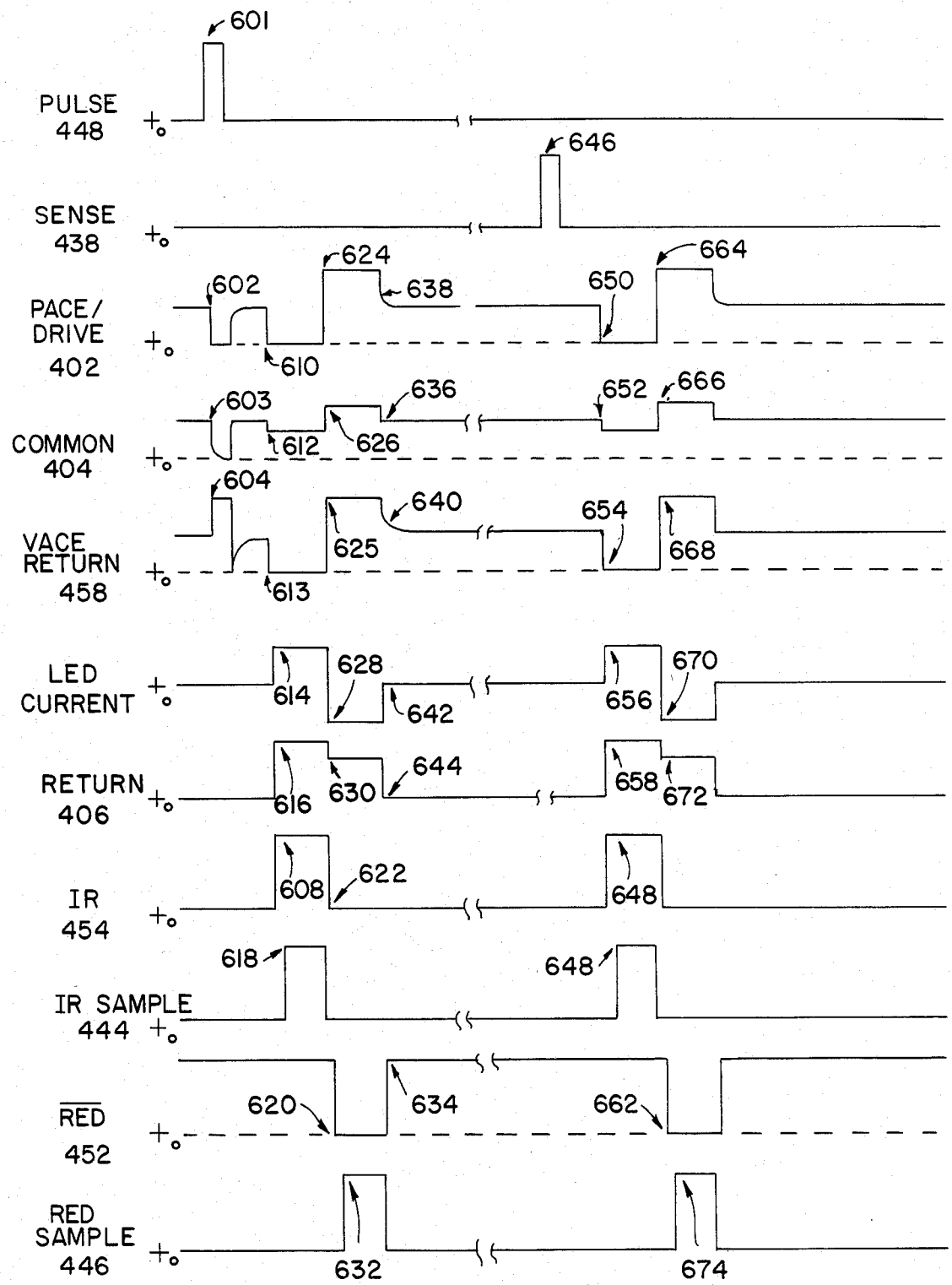
FIG. 10 is a timing diagram illustrating the operation of the sensor capsule, and its relation to the operation of the cardiac pacemaker with which it is intended to be employed.

FIG. 9 shows a schematic of the analog portions of the circuitry illustrated in FIG. 7, including the current mirror 416, the current driver 414, the voltage/pacing driver 412, the pacing return amp 422 and the red and IR sample and hold circuitry 418 and 420, respectively. The current and voltage regulator circuits used in the current driver 414 and voltage pacing driver 412 are based upon a common design often found in audio power amplifier output stages. The operation of the circuitry in FIG. 9 is best understood in conjunction with the timing diagram of FIG. 10. In the following description, all reference numbers of 600 or higher refer to FIG. 10. Starting with a pace signal 600 indicating time out of the escape interval of the pacemaker, on line 448, the pacing return amp 422 is activated. The pace signal 600 applies a current across LED 542 via resistor 544, which activates phototransistor 552 which turns on transistor 548 driving PACE RETURN line 458 high at 604 and simultaneously driving PACE DRIVE line 402 low via transistor 540, allowing discharge of output capacitor 554 through transistor 548, PACE RETURN line 458, electrode 424 (FIG. 7), electrode 420 (FIG. 7), PACE DRIVE line 402 and transistor 540. In addition, as discussed in conjunction with FIG. 8, above, the pace signal 600 also takes the reset off decade counter 462 which begins the timing of the sensing cycle. After the pace signal 600, the Q output of flip-flop 466 (FIG. 8) goes high, driving IR line 454 high at 608, turning on transistors 536 and 540, driving PACE/DRIVE line 402 low at 610 and turning on transistors 512 and 508 providing current flow through the infrared diode 236 (FIG. 7) of approximately 20 milliamps at 614. COMMON line 404 goes to one LED drop above ground at 612. This in turn triggers current flow 616 through phototransistor 234 (FIG. 7) and which, via RETURN line 406 is applied to current mirror 416. The current mirror comprising transistors 500, 502 and resistor 504 generates an output signal on line 456. During counts 2-4 of decade counter 462 (FIG. 8), the IR SAMPLE line 444 goes high at 618, allowing the output of current mirror 416 on line 456 to be sampled by the IR sample and hold circuitry 418. The IR sample and hold circuitry consists of an analog switch 558 which, when activated by a signal on IR SAMPLE line 444 passes the voltage on line 456 to op amp 568 and capacitor 562. The sample and hold system does not operate in the classical sense of sampling until the hold capacitor 562 reaches the exact input voltage. Instead, the sample time is only a small fraction of the time constant of the source resistance and the holding capacitor 562. In this way, in response to any abrupt voltage swings on line 456, the capacitor 562 swings only part way to the final value during each sample, but after a series of samples will converge on the actual source voltage value. This mode of operation is believed appropriate in that the oxygen saturation level changes between successive sample is small compared to the overall capacity of capacitor 562. This approach has the advantage that it minimizes power consumption and circuit complexity.

On the fifth clock cycle counted by decade counter 462 (FIG. 8), the RED line 452 goes low at 620 and the IR line 454 goes low at 622. This change turns off transistors 540 and 536 in the voltage/pacing driver 412 and turns on transistors 532 and 534, sending the PACE/DRIVE line 402 high at 624. In addition, transistors 508 and 512 are turned off while transistors 518 and 522 are turned on applying LED current of the opposite polarity of approximately 20 milliamps at 628 across red LED 536. COMMON line 004 goes to one LED drop below battery voltage at 626. Light reflected from red LED 236 allows current to flow through phototransistor 234 at 630, which, via RETURN line 406 and current mirror 416 provides a proportional voltage on line 456. During counts 6, 7 and 8 of decade counter 462, the RED SAMPLE line 446 goes high at 632, enabling the red sample and hold circuitry 420, which includes an analog switch 556, capacitor 560 and an op amp 566, which function in a fashion identical to that of the circuitry discussed in conjunction with the IR sample and hold circuitry 418. Due to the high impedance of the pacing return amp 422 when inactive, the voltage on PACE RETURN line 458 follow the voltage on PACE/DRIVE line 402, preventing current flow between electrode 410 (FIG. 7) and electrode 424 (FIG. 7).

In order for the specific embodiment of circuitry illustrated to function properly, it is necessary that high efficiency LED's be used which preferably limit voltage across the LED's to approximately 1.6 volts. This places COMMON line 40 at approximately 1.6 volts during operation of LED 236 and at approximately 2.0 volts during operation of LED 238. This assures adequate bias for phototransistor 234.

As noted above, the voltage on COMMON line 404 changes at the point LED 238 is turned on. Because phototransistor 234 has a large collector-base capacitance if the voltage across collector and emitter decreases, transistor 234 will temporarily shut off for a period long enough to discharge this capacitance. Therefore, the circuitry herein has been arranged to provide an increase in voltage, rather than a decrease, at the point the voltage on COMMON line 404 changes. Transients due to the COMMON line 404 voltage change do not appear to be significant at light levels generated by high efficiency LED's as described herein.

The voltages on RED OUT line 432 and IR OUT line 430 are fed to the IR/R division network 428 to produce an analog DC voltage signal on line 434 (FIG. 7) indicative of oxygen saturation. This signal on line 434 is provided to sensor processing circuitry 30 (FIG. 1) and used to regulate the escape interval of the pacemaker as described above.

Similarly, after the signal 646 on SENSE line 438, IR line 454 goes high at 658 causing PACE/DRIVE line 402 to go low at 650 providing a current of approximately 20 milliamps at 656 across IR diode 538. COMMON line 402 goes to an LED drop above ground at 654. This allows a current to flow through photo transistor 534 at 658 which is sampled while the IR SAMPLE line 444 is high at 660. Halfway through the sampling cycle at the count of 5 on the decade counter 462 (FIG. 8), RED line 452 goes low at 662, along with IR line 454, driving PACE/DRIVE line 402 high at 664 and allowing a current of approximately 20 milliamps at 670 to flow across the red diode 238 (FIG. 7). COMMON line 404 goes to one LED drop below battery voltage at 666. Light received from red diode 238 (FIG. 7) allows current to flow through photo transistor 234 (FIG. 7) at 672, which is sampled while RED SAMPLE line 446 is high, at 674. Again, the voltage on PACE RETURN line 458 follows the voltage on PACE/DRIVE line 402, avoiding current flow between tip electrode 410 (FIG. 7) and electrode 424 (FIG. 7).

The following components were used to construct the circuitry illustrated in FIGS. 7, 8 and 9:

| Resistors | Value(Ω) | Transistors | Type |
| --- | --- | --- | --- |
| 504 | 10K | 500 | 2N2907 |
| 506 | 5.6K | 502 | 2N2907 |
| 510 | 33 | 508 | 2N2907 |
| 514 | 1K | 512 | 2N2907 |
| 516 | 1K | 518 | 2N2222 |
| 520 | 33 | 522 | 2N2222 |
| 524 | 5.6K | 530 | 2N2907 |
| 526 | 5.6K | 532 | 2N2907 |
| 528 | 5.6K | 536 | 2N2222 |
| 530 | 27K | 540 | 2N2222 |
| 538 | 27K | 542/552 | SPX-33 |
| 544 | 330 |  | Opto-Isolator |
|  |  | 234 | Stanley |

-continued

| Integrated Circuits | Types | Capacitors | SPS-201 Phototransistor Value(mF) |
|---|---|---|---|
| 462 | RCA CD4017 | 554 | 10 |
| 466 | RCA CD4013 | 560 | .1 |
| 468 | RCA CD4071 | 562 | .1 |
| 472 | RCA CD4081 | | |
| 476 | RCA CD4075 | Diodes | Type |
| 482 | RCA CD4075 | 236 | Optron OPC-123 IR LED |
| 556 | RCA CD4066 | | |
| 558 | RCA CD4066 | 238 | Stanley HIK Red LED |
| 566 | Intersil 7621 | | |
| 568 | Intersil 7621 | | |

The particular circuitry disclosed in FIGS. 8 and 9 is optimized for use with a lithium thionylchloride battery providing a supply voltage of 3.6 volts. However, functionally similar circuitry adapted for use with batteries of other voltages is believed to be within the scope of the present invention. In addition, in those embodiments in which lower voltage batteries are used, it may be desirable to incorporate a voltage doubler in the pacing return amplifier, in order to provide adequate voltage to capture the heart. The present invention is also believed broad enough to encompass such embodiments. It is also acknowledged that there are numerous alternative ways of providing the time periods provided by the circuitry of FIG. 8, and other analog and/or digital equivalents of this circuitry are believed to also be within the scope of the present invention.

In conjunction with the above written specification and drawings, we claim:

1. An implantable lead comprising:
a sensor capsule having an interior, an exterior surface, a proximal end and a distal end, said sensor capsule comprising a unitary conductive sensor body extending the length of said sensor capsule and exposed to the exterior of said sensor capsule at the proximal and distal ends of said sensor capsule, said sensor capsule further comprising a transparent tubular member, surrounding said sensor body, said tubular member allowing passage of light into the interior of said sensor capsule;
electronic circuitry means for sensor capsule;
electronic circuitry means for sensing a physiologic parameter of the blood by sensing light reflected from said blood, said circuitry means mounted within the interior of said sensor capsule and electrically coupled to said sensor body;
first electrical conductor having a proximal end and a distal end, the distal end of said first conductor coupled to said sensor body at the proximal end of said sensor capsule exterior to the interior of said sensor capsule, the proximal end of said first conductor extending proximally from said sensor capsule;
second electrical conductor, insulated from said first circuitry means;
third electrical conductor having a proximal end and a distal end, the proximal end of said third conductor electrically coupled to said sensor body at the distal and of said sensor capsule exterior to the interior of said sensor capsule, the distal end of said third conductor extending distally from said sensor capsule;
electrode coupled to said third conductor; and
elongated insulative lead body enclosing said first and second conductors, said sensor capsule and said third conductor, said electrode exposed to the exterior of said insulative lead body.

2. A lead according to claim 1 wherein said electronic circuitry means comprises a reflectance oximeter and wherein said insulative lead body is transparent to visible and infrared light.

3. An implantable lead comprising:
a sensor capsule having an interior, an exterior surface, a proximal end and a distal end, said sensor capsule comprising a unitary, conductive sensor body extending the length of said sensor capsule and exposed to the exterior of said sensor capsule at the proximal and distal ends of said sensor capsule;
electronic circuitry means for sensing a physiological parameter of the blood stream, mounted within said sensor capsule and electrically coupled to said sensor body;
first electrical conductor extending proximally from said sensor capsule and electrically coupled to said sensor body at the proximal end of said sensor capsule;
second electrical conductor, insulated from said first conductor and extending proximally from the proximal end of said sensor capsule, said second conductor extending into the interior of said sensor capsule and electrically coupled to said circuitry means;
a third electrical conductor electrically coupled to said sensor body at the digital end of said sensor capsule and extending distally from said sensor capsule;
a fourth electrical conductor, extending proximally from the proximal end of said sensor capsule and extending into the interior of said sensor capsule, insulated from said sensor body and coupled to said circuitry means;
elongated insulative lead body enclosing said first, second and fourth conductors, said sensor capsule and said third conductor with said electrode exposed to the exterior of said insulative lead body; and
wherein said circuitry means comprises a two wavelength reflectance oximeter.

4. An implantable lead comprising:
a sensor capsule having an interior, an exterior surface, a proximal end and a distal end, said sensor capsule comprising a unitary conductive sensor body extending the length of said sensor capsule and exposed to the exterior of said sensor capsule at the proximal and distal ends of said sensor capsule;
electronic circuitry means for sensing a physiological parameter of the blood stream, mounted within said sensor capsule and electrically coupled to said sensor body;
first elongated electrical conductor extending proximally from said sensor capsule and electrically coupled to said sensor body at the proximal end of said sensor capsule;
second elongated conductor, insulated from said first conductor and extending proximally form the proximal end of said sensor capsule, said second conductor extending into the interior of said sensor capsule and electrically coupled to said circuitry means;

a third conductor electrically coupled to said sensor body at the distal end of said sensor capsule and extending distally from said sensor capsule;

a fourth conductor, extending proximally from the proximal end of said sensor capsule and extending into the interior of said sensor capsule, insluated from said sensor body and coupled to said circuitry means;

elongated insulative lead body enclosing said first, second and fourth conductors, said sensor capsule and said third conductor with said electrode exposed to the exterior of said insulative lead body; and wherein said electronic circuitry means comprises a two wavelength reflectance oximeter and wherein said circuitry means comprises:

first light emitting diode electrically coupled between said sensor body and said second conductor;

second light emitting diode electrically coupled between said sensor body and said second conductor parallel to but at an opposite polarity to said first light emitting diode; and a phototransistor coupled between said second and fourth conductors and insulated from said sensor body.

5. A lead according to claim 3 or claim 4 wherein said first conductor comprises an elongated coil conductor having an interior lumen and wherein said second and fourth conductors are located within the lumen of said first conductor.

* * * * *